(12) United States Patent  
Keen (10) Patent No.: US 7,574,452 B2  
(45) Date of Patent: Aug. 11, 2009

(54) TRANSACTIONAL STORAGE AND WORKFLOW ROUTING FOR MEDICAL IMAGE OBJECTS

(75) Inventor: Ronald Keen, Shelburne, VT (US)

(73) Assignee: General Electric Company, Schenectady, NY (US)

( * ) Notice: Subject to any disclaimer, the term of this patent is extended or adjusted under 35 U.S.C. 154(b) by 169 days.

(21) Appl. No.: 11/288,956

(22) Filed: Nov. 28, 2005

(65) Prior Publication Data

US 2008/0016111 A1   Jan. 17, 2008

(51) Int. Cl.
*G06F 7/00* (2006.01)
*G06F 17/00* (2006.01)

(52) U.S. Cl. .................. 707/104.1; 707/1; 707/10; 707/200; 707/204; 382/130; 382/305

(58) Field of Classification Search ........ 707/1–10, 707/100–104.1, 200–206; 705/2, 3, 37; 709/229; 382/128, 132, 130, 140, 216, 254, 260, 276, 382/282–296, 305, 307
See application file for complete search history.

(56) References Cited

U.S. PATENT DOCUMENTS 6,529,757 B1 *   3/2003   Patel et al. .................. 600/407
6,662,198 B2 *   12/2003  Satyanarayanan et al. ... 707/204
2004/0141661 A1 *   7/2004   Hanna et al. ................. 382/305

OTHER PUBLICATIONS

Wong S.T.C., A hospital integrated framework for multimodality image base management, Jul. 1996, IEEE, 455-469.*

Nilsson A.A., A queueing model of picture archiving and communication system (PACS) with a hierarchy of storage, Jun. 3-6, 1990, IEEE, 1-8.*

Metzler V., A novel object-oriented approach to image analysis and retrieval, IEEE, Apr. 7-9, 2002, 14-18.*

* cited by examiner

*Primary Examiner*—Jean B Fleurantin
(74) *Attorney, Agent, or Firm*—Andrus, Sceales, Starke & Sawall, LLP (57) ABSTRACT

A Picture Archiving and Communications System (PACS) implements medical image, video, and medical record storage, retrieval and archiving with transactional processing having properties of atomicity, consistency, isolation and durability (ACID). A two-phase commit procedure is used to prevent data corruption. Relational database storage of image objects permits images to be stored in a manner that allows a user to determine the quality and other characteristics of the image.

11 Claims, 11 Drawing Sheets

| Image ID | Patient ID | Image | Color Depth | Last Edited | Version Of | Version Num. |
|---|---|---|---|---|---|---|
| 1 | 1 | [binary data] | 16 | 1/1/05 | | 1 |
| 2 | 2 | [binary data] | 24 | 5/1/05 | | 1 |
| 3 | 1 | [binary data] | 16 | 2/3/05 | 1 | 2 |
| 4 | 1 | [binary data] | 16 | 3/5/05 | 1 | 3 |
| 5 | 3 | [binary data] | 32 | 4/10/05 | | 1 |

TRANSACTIONAL STORAGE AND WORKFLOW ROUTING FOR MEDICAL IMAGE OBJECTS

BACKGROUND OF THE INVENTION

1. Field of the Invention

This invention relates generally to the storage, archiving, and retrieval of medical images and video, and more particularly to improvements in a Picture Archiving and Communications System (PACS), providing to such systems ACID (atomicity, consistency, isolation, and durability) characteristics as well as versioning and other reliability enhancing features within the context of the medical image objects.

2. Description of the Related Arts

A PACS is a system for the storage, retrieval, and display of medical images. A PACS typically consists of one or more networked computers along with a substantial amount of semi-permanent digital storage in the form of, for instance, a RAID (redundant array of inexpensive hard disks), tape storage, or optical disks. A PACS also typically includes software for storing, retrieving, and displaying images, along with hardware that may be necessary for physical management of digital media (e.g., a robotic tape loader), display, and input.

A PACS is typically connected to an imaging device such as a CT (computerized tomography) scanner, an MRI (magnetic resonance imaging) scanner, or an X-ray machine capable of providing images in digital format, often including images compliant with the DICOM (digital imaging and communications in medicine) format. A doctor or other health care provider uses the imaging device to create a digital picture of a patient for diagnosis or treatment purposes. The image is delivered via a network to the PACS, where it is stored along with information identifying the particular patient. The image is viewed on the PACS immediately or it is retrieved for display later. The image is optionally processed prior to storage, or it is stored in a raw digital format and subjected to optional processing later.

Prior to the development of PACS technology, hospitals typically stored medical images on film that had to be catalogued and retrieved by hand. Early computerized medical imaging devices were flawed because the machines were typically standalone devices with no or limited archival capabilities and proprietary file formats. PACS, along with the standard DICOM and other file formats, provided a convenient, standardized way to store medical images with fast, electronic retrieval, more convenient backup, and potential for remote electronic distribution.

Despite their advantages, traditional PACSs have numerous shortcomings. First, a traditional PACS stores images, but does not store other non-graphical components of a patient's medical record such as diagnoses, examination notes, etc. Storing exam notes and other parts of the record separately from the images increases the chance that the records and images will become out-of-sync. If the PACS does store non-graphical components of the medical record, or stores ancillary information about the images such as patient name, exam, timestamp or image size, it typically does so in a relational database. However, the images themselves are typically stored on the file system of a computer rather than in the database. Because standard file systems are not protected by the two-phase commit procedure or other established ACID standards that guarantee transactional integrity in a modern relational database, an update might succeed on the medical record or ancillary information but fail on the image, or vice-versa. The record or ancillary information would then be out-of-sync with the image. Complex reconciliation algorithms might be necessary to ensure that records and images are in sync, as this type of processing lacks synchronicity. The lack of guaranteed transactional integrity between the file system and indexed information is compounded when images, records, and ancillary information are manipulated by backup, caching, and migration processes. Providing a widely-understood programmatic means of guaranteeing transactional integrity across both the medical image objects and the information about them through a commit/rollback procedure would greatly improve robustness and improve the safety of automated PACS procedures, while avoiding maintenance procedures. Medical image storage in current PACSs is not performed in a manner that ensures ACID characteristics such as can be provided by database storage using two-phase commit.

Next, storing images in the file system(s) makes it difficult to build a distributed PACS. A relational database package may operate in a distributed fashion, automatically hiding the distributed nature of the system from the user and providing a single integrated "view" of the database. Storing the entirety of the medical data, including metadata and images, in a relational database would therefore allow for simpler creation of a distributed PACS.

Further, file systems are vulnerable to virus attacks. Relational databases provide a greater level of protection against viruses. Thus, a PACS that stores its images in a relational database provides an inherent shield against viruses that might otherwise corrupt the image files. File systems are also vulnerable to unauthorized access: a hacker might obtain access to a PACS and view a patient's records without authorization. While a relational database cannot provide complete protection against unauthorized access, most databases provide an authentication system and store their data in an obfuscated format such as Oracle's varBinary format and SQL-Server 2005's two-way x509 encryption. Storing images in a relational database therefore provides protection against unauthorized access.

Additionally, where images are stored "naked" in the file system, they may be easily manipulated by other processes without the knowledge of the database. For instance, an image might be accessed and cropped by a process outside the database. The image size and last-edited date stored in the database would then be incorrect. This could be a problem for several reasons. For example, some diagnostic procedures might require images of a certain size. Users who tried to run the procedure on images whose actual size differed from that recorded in the database would encounter an unexpected and perplexing error. For another example, a doctor relying on an erroneous last-edited date could have an incorrect understanding of the speed of progression of a disease. Moving the medical images into the database forces all image manipulation to go through the database. Processes within the database (such as Oracle PL/SQL routines) may then be run automatically in response to all image updates to ensure that ancillary information about the image is kept up-to-date. The image cannot be altered without the database knowing about it, and the user need not worry about manually updating other records such as image size or date of last alteration. Another concern if the images are not controlled through the database is legal compliance, as HIPAA provisions may be violated under approaches that do not provide robust auditing of image access and manipulation.

More generally, lack of integration of image information with a single database system raises various concerns with respect to reconciling exceptions, ensuring that information remains up-to-date, general transactional integrity and the like. Broadly speaking, lack of integration means that identical or related information is located in two places, which inherently introduces risk and complexity.

Prior art PACSs do not disclose remedies for these problems. Systems are known to integrate display of both medical images and non-graphical elements of a patient's medical record such as diagnoses and examination notes. For instance, U.S. Pat. No. 6,434,569 discloses a system for combining a patient's medical record and images on one display. But such systems do not integrate the storage of the disparate sets of data. Nor do such systems provide two-phase commit to guarantee that information updates have ACID characteristics. Thus, such systems may allow images and non-graphical data to get out-of-sync.

U.S. Pat. No. 5,272,625 discloses a medical image management system comprising multiple databases storing medical images, with one directory server tracking which patients' images are stored on which databases. The patent does not disclose a relational database with two-phase commit to guarantee that updates of images and non-graphical data are atomic. This is significant, again, primarily because lack of atomicity may allow images and non-graphical data to get out-of-sync or be corrupted by concurrent updates by other processes. Nor does the patent disclose a system in which, because images are stored in database tables rather than the file system, the database software might elect to store the images in multiple sets of blocks across multiple database servers without altering the appearance of contiguous data storage to the user. This limits the known PACS to potentially inefficient use of disk space and network bandwidth.

U.S. Pat. No. 6,529,757 describes a PACS in which images are processed to varying degrees before being stored in a database. Again, the patent does not disclose storing the images in a relational database with two-phase commit. The multi-stage processing disclosed in the patent stores only one instance of the preprocessed image rather than multiple instances of the same image or images of the same body part taken at different times. Thus, it does not allow doctors to easily track the progression of diseases or healing through a series of images or allow for robust editing of images and correction of errors.

Therefore, there is a need for a PACS capable of storing image data in a relational database with transactional integrity guaranteed by two-phase commit. There is also a need for a PACS capable of storing both images and non-image data such as examination notes and a medical record in the same database.

SUMMARY OF THE INVENTION

To address the above problems with traditional picture archiving and communications systems, the present invention provides a PACS that implements medical image, video, and medical record storage, retrieval, and archiving with ACID properties.

In one embodiment, upon acquisition of the medical image from the imaging device, an attempt is made to store the image in a database using a 2-phase commit. An exception causes the transaction to be rolled back and other steps to be taken, such as notifying the user or attempting to store the image again. The 2-phase commit procedure guarantees that data is locked during the transaction, making the transaction atomic and protecting the data against concurrent modification by other processes.

In a further aspect of the invention, following successful storage of the image, the entire database or, optionally, simply the altered portion of the database, is replicated for backup, remote access, or other purposes including efficient retrieval from multiple geographically-remote nodes. Replication of portions or the entirety of the database also facilitates scaling, with each node having processing of data corresponding to that node while still remaining integrated with the overall system (i.e., a "federated" model).

In another aspect of the invention, the system stores still images or motion video in formats such as JPEG 2000 or MPEG along with any corresponding audio. In various embodiments, facilities are provided to store the images, video, and audio in the database in conventional formats such as varBinary format on an Oracle/SQL-Server database. Facilities are provided to stream the video for viewing on other computers or terminals.

In yet another aspect of the invention, the database consists of more than one server. The servers are optionally geographically distributed and linked via a computer network such as a WAN (wide area network) or the Internet. The user is provided an integrated "view" of the plurality of servers such that the existence of multiple underlying computers is invisible to the user, per the "federated" approach referenced above.

In another aspect of the invention, the database software provides auditing. Information about additions, deletions, reads, and changes to the images and other data—such as who made the changes and when, and what was changed—is recorded. The information is made available for subsequent security investigations or other purposes, e.g., HIPAA auditing.

In another aspect of the invention, along with the image data itself the database stores "meta-data" about the image, such as the amount of data (e.g., size in kilobytes, megabytes or other format), the image size (e.g., height and width), and when the image was created. Optionally, a system in accordance with the invention also stores non-image data such as the patient's examination record in the database. Alterations to the meta-data and non-image data are executed in the same transaction as the image data. Since alterations are protected by two-phase commit, the image data, meta-data, and non-image data are always changed in an atomic transaction. Therefore, they never become out-of-sync and are never corrupted by concurrent updates executed by another process.

In another aspect of the invention, facilities are provided for versioning of images. A patient may, for example, return to the doctor for a second CT scan to determine how well treatment is progressing. When adding the second CT scan to the PACS, the doctor has the ability to indicate that the second image is a new version of the old image. The old image is not deleted. The new image is added as well as data indicating the version relationship between the images. A user then has the ability to retrieve the multiple versions of the CT image, viewing them in a slide show, for instance. Additionally, the old image is preserved in case the new image has errors.

In another aspect of the invention, facilities are provided to perform backup on a scheduled or ad hoc basis. Backup is available in modes including a complete clone of the data (a snapshot), or incremental mode, containing only those data blocks changed since the last backup. A user is provided the ability to restore the PACS data after a system failure as well as to rewind the PACS to a prior point in time for disaster recovery or testing.

In another aspect of the invention, control over access to the images and other data in the PACS is provided. Authentication is required before a user is allowed to view or update data. The ability to restrict access to only to certain users is typically provided by access-control lists and, depending on the situation, other suitable measures. Facilities are also provided to assign certain "degrees" of access rights. For instance, certain users are allowed only to view certain data, while other users are allowed to edit the data.

The features and advantages described in the specification are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The invention has other advantages and features which will be more readily apparent from the following detailed description of preferred embodiments of the invention and the appended claims, when taken in conjunction with the accompanying drawings, in which:

DETAILED DESCRIPTION OF THE PREFERRED EMBODIMENTS

The Figures and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

The present invention includes a system and method for providing medical image management in a PACS. In preferred embodiments, full auditing is provided with 2-phase commit processing using relational database storage for medical objects. Horizontal replication is employed to partition information. The system allows for incremental backups of blocks changed, as opposed to requiring file system backups. The system implements version imaging; provides authentication support, rights management, geographically distributed deployment, encryption and access control; supports WADO, XDS and traditional DICOM part-10 file system as well as DICOM SCP/SCU formats; isolates images from external changes, such as from viruses or other malicious attacks; obfuscates data by its internal structure using symmetric encryption to prevent unauthorized manipulation of or access to data; provides a simple mechanism for reconciling patient demographics as well as procedure information; facilitates splitting/merging studies based on the relational audit trail and transactional nature of processing; includes mechanisms to ensure robust processing such as snapshot mirrors and built-in failover; and supports business continuity through support of shared-nothing mirrors.

Figure 1:
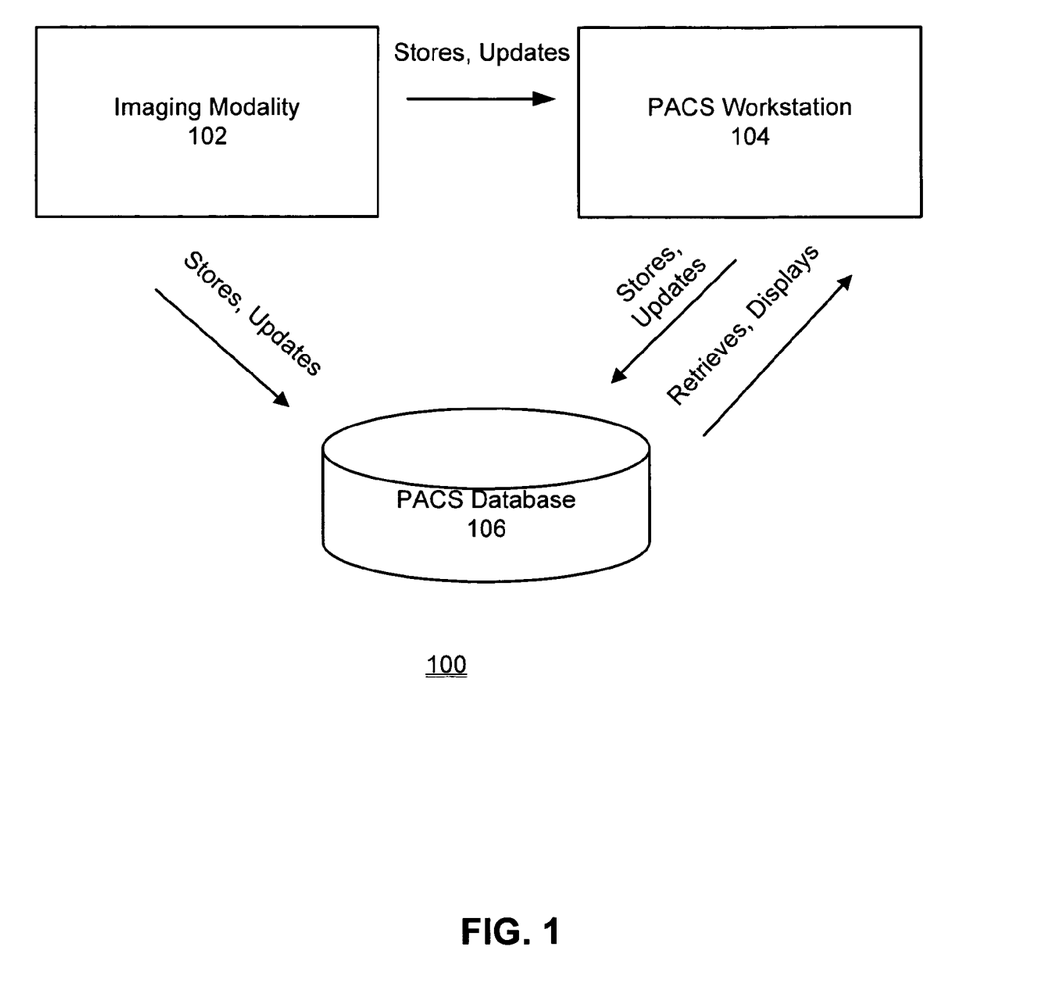
FIG. 1 illustrates in overview fashion interaction among basic components of a system in accordance with the present invention.

Referring now to FIG. 1, a system 100 in accordance with the present invention is shown by way of its basic components: an imaging modality subsystem 102, a PACS workstation 104, and a PACS database 106. System 100 is configured, as shown, to permit imaging modality 102 to store and update information in both PACS workstation 104 and PACS database 106, typically communicating directly with a DICOM Acquisition process. PACS workstation 104 also stores and updates information in PACS database 106, and PACS database 106 sends information to PACS workstation 104 to allow a user to retrieve and display such information. In one embodiment, for example, conventional streaming is used to provide image information from PACS database 106 to PACS workstation 104. In a typical embodiment, each of imaging modality subsystem 102, PACS workstation 104 and PACS database may be composed of a number of distributed elements. For example, imaging modality subsystem 102 in a typical embodiment includes a number of imaging modalities, including X-ray and magnetic resonance imaging devices. Likewise, in a typical embodiment system 100 is implemented with a number of DICOM Acquisition processes, distributed PACS workstations 104 and PACS databases 106. As more fully described below, system 100 coordinates and controls these various components to provide the features described herein.

Figure 2:
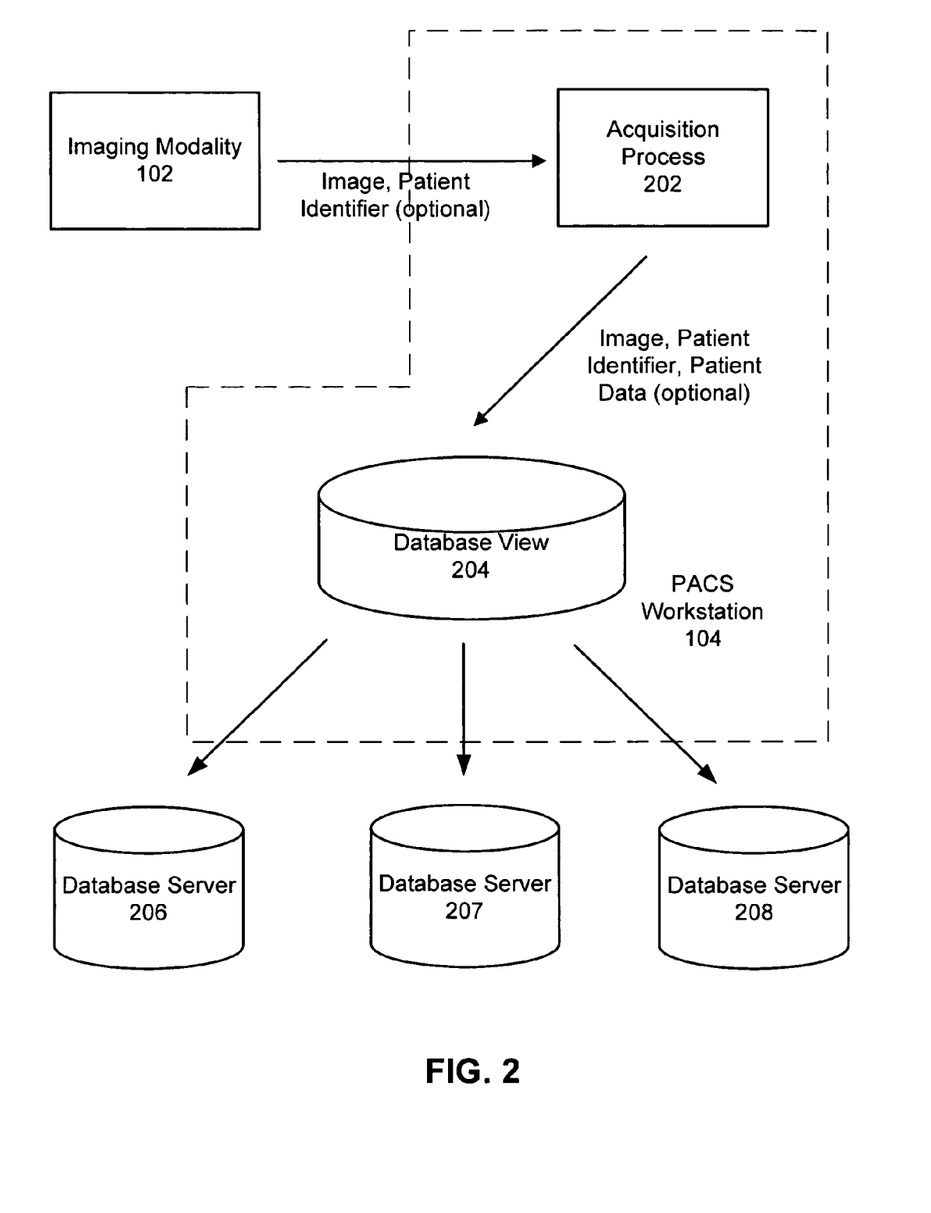
FIG. 2 details the PACS workstation and database components shown in FIG. 1.

Referring now to FIG. 2, more detail is provided concerning the structure and operation of system 100. Specifically, PACS workstation 104 includes an acquisition process subsystem 202 and a database view subsystem 204. Acquisition process subsystem 202 accepts as input image information, e.g., medical image objects, from imaging modality subsystem 102 and, in a preferred embodiment, corresponding patient identification information as well. In typical embodiments, subsystem 202 is a separate process from PACS workstation 104, while in some embodiments it is run on PACS workstation 104. In some embodiments, this patient information comes directly from imaging modality subsystem 102, while in other embodiments, the patient information comes from other storage locations, databases, or is input directly by the user of PACS workstation 104. Acquisition process 202 then transacts the meta-data, patient information and image data into the relational database. Database view subsystem 204 provides read-only views for PACS workstation 104. The view is typically for caching the information and provides a proxy for the storage/database server, alleviating the need for all concurrent users to access the single source of the images. Using PACS workstation 104, a clinician, radiologist or other user typically annotates, marks up and otherwise processes information relating to medical images.

In a preferred embodiment, the processed image and patient information is then sent to database servers 206-208. In one configuration, these multiple database servers provide redundant storage of information for backup purposes. In another configuration, the multiple database servers each store portions of the information to provide additional redundancy for business continuity and the multiple copies allow for scalability and concurrency of the solution.

Figure 3:
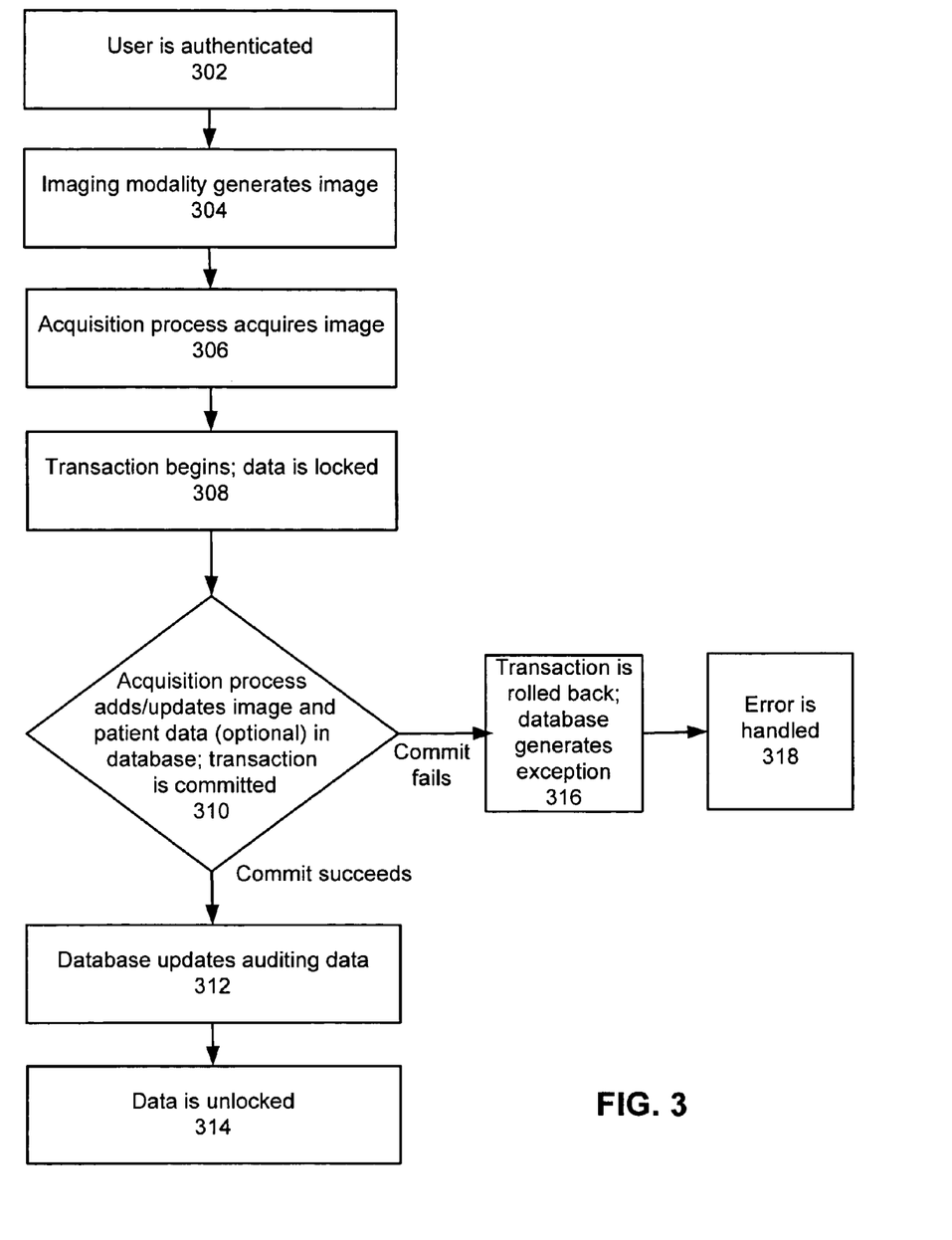
FIG. 3 illustrates an image storage workflow in accordance with the present invention.

Referring now to FIG. 3, a typical workflow in accordance with a preferred embodiment is shown. A user of system 100 is first authenticated 302, after which an appropriate imaging modality subsystem 102 is used to generate 304 a medical image object, either with or without corresponding patient information. Next, acquisition process subsystem 202 acquires 306 the image object and begins 308 processing by first "locking" the acquired data to ensure data integrity. At this point, if additional corresponding patient information is available to be associated with the acquired information it is added, and acquisition process subsystem 202 attempts to store the information in local transaction storage (e.g., database view subsystem 204) using conventional two-phase commit processing. A check 310 is made to see whether the two-phase commit was successful. If not, the transaction is rolled back, i.e., the data is captured as an error/exception, but the image and patient information is not considered usable for interpretation because of the error (which could be simple as the MRN for the Patient not matching the MRN in the medical image) and database view subsystem generates 316 an exception, leading to appropriate error handling 318. In a preferred embodiment, error handling 318 includes storing the image anyway, along with a note that two-phase commit processing was unsuccessful, storing uncertain patient information with a flag that such information may not be trustworthy, rejecting the image information entirely, or taking other action, depending on the use to which system 100 is being put. For example, if system 100 is being used to store critical information such as radiology information system or an electronic health record, then any information below a particular usability threshold (e.g., a minimum resolution for x-ray images) is outright rejected. However, if the system 100 is being used to collect and store general medical histories for patients, all images regardless of their parameters and the success of two-phase commit may be stored, with an annotation being made in each case of the robustness of each stored image.

If check 310 indicates that the two-phase commit succeeded, database view subsystem 204 is updated 312 with the auditing data, e.g., rules such as validity of the image being a true DICOM study, if the patient information in the Study matches patient demographics in the information system, and the image data are unlocked 314 for transmission to permanent storage.

Figure 4:
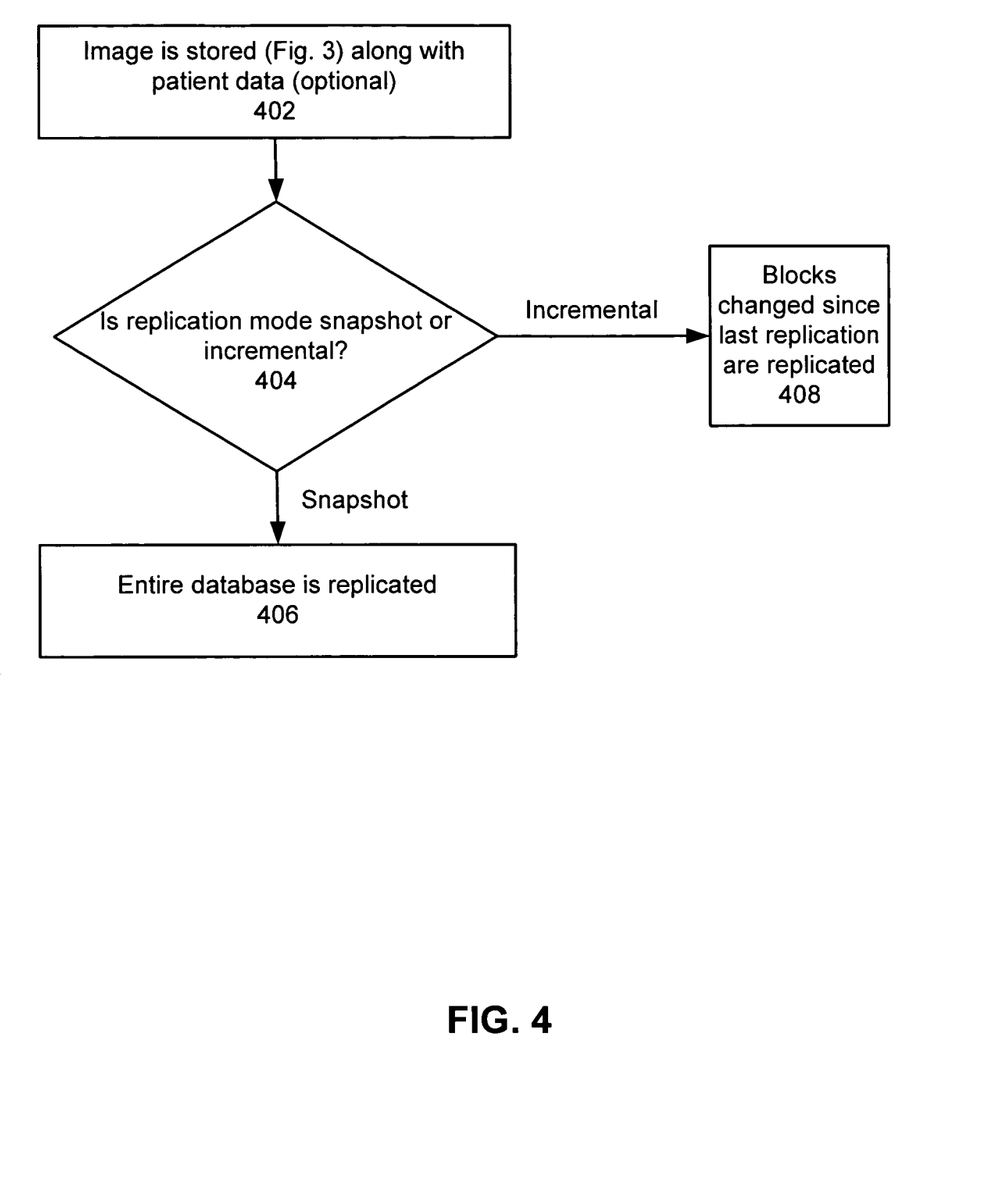
FIG. 4 illustrates replication of PACS database workflow in accordance with the present invention.

Referring now to FIG. 4, processing continues from initial storage 402 of the image and any corresponding patient data to a check 404 as to the type of further storage required, in this example whether replication is to be snapshot or incremental. In various embodiments of the invention, this processing addresses a wide range of storage options, including partitioning, versioning, authentication, rights management, geographic distribution, mirroring or other redundant storage, encryption, and merging/splitting with other imaging studies. For purposes of illustration, FIG. 4 is limited to replication mode checking. If incremental replication is to be performed, processing replicates 408 only those blocks that were changed since the last replication. If snapshot replication is called for, the entire database is replicated 406. In various embodiments, this stage of processing includes streaming image data to a rendering/viewing subsystem, converting it to standard storage formats (e.g., DICOM), or distributing it to various database servers, e.g., servers 206-208, depending on a particular facility's needs for business continuity and performance as well as the extent to which replication/mirroring of images stored in the relational database, and corresponding rules for access, can address those needs.

Figure 5:
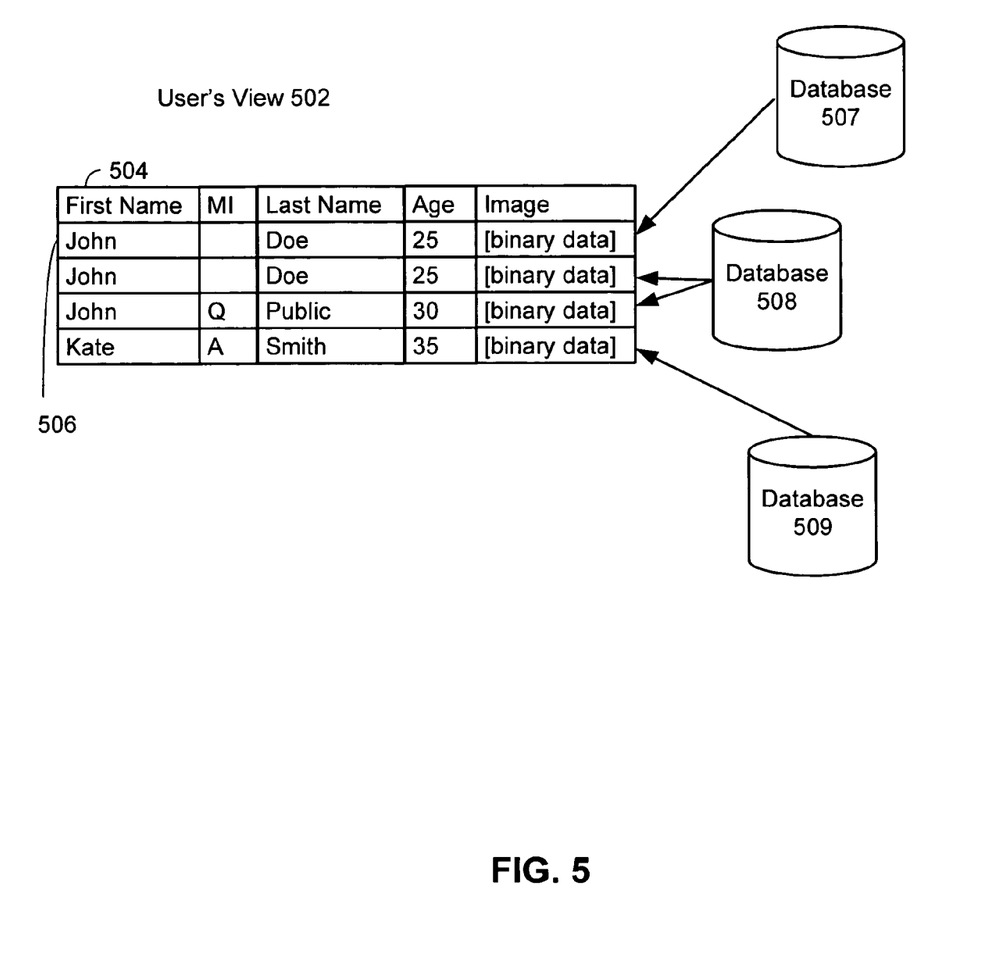
FIG. 5 illustrates use of distributed databases in accordance with the present invention.

Referring now to FIG. 5, there is illustrated the distributed nature of data on which system 100 operates. A user's view 502 includes, in one embodiment, columns with type of information (e.g., First Name 504) and rows with specific patient information (e.g., "John") as well as information corresponding to various organizations (e.g., hospitals) and locations (e.g., "Old Wing") corresponding to particular images for each patient. Such information is not necessarily physically stored in all locations; as illustrated in FIG. 5 several databases 507-509 are used in this instance to provide patient-related information. These databases are capable of having differing levels of robustness, and system 100 is configured to allow use of all pertinent data while maintaining knowledge of the robustness of the information being used. The relational catalog/index of all patients and images are replicated in relational format for performance and business continuity. The medical images, i.e., binary data, can be replicated in partitions, for instance horizontal partitioning providing all images for a particular facility (All images for Organization-a etc . . . ) In one embodiment, two databases 507, 508 contain image and patient data for the same patient, and a caregiver is able to determine the trustworthiness of the data in each instance.

Figure 6:
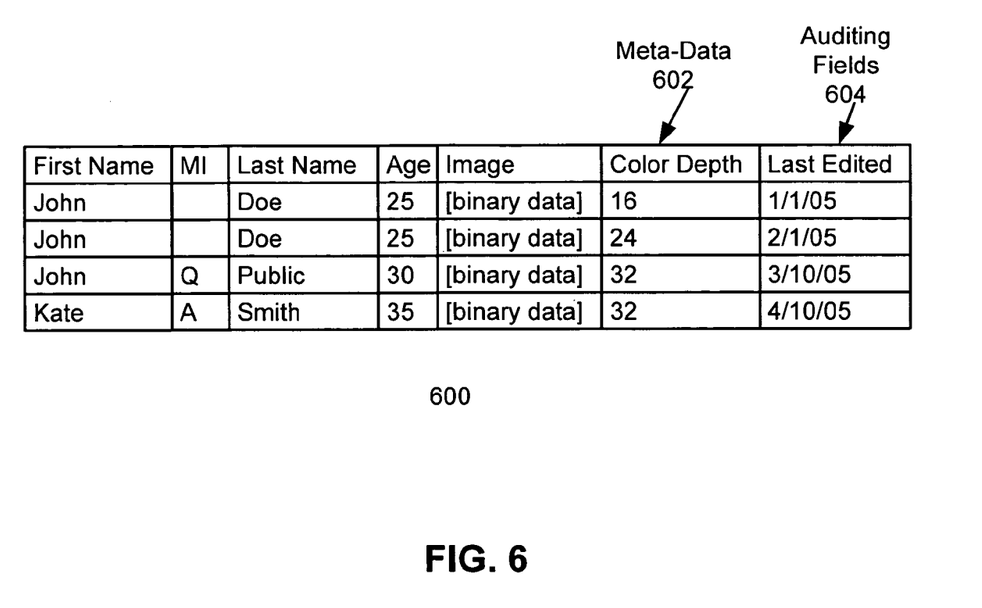
FIG. 6 illustrates use of meta data and auditing fields in accordance with the present invention.

Referring additionally now to FIG. 6, there is illustrated an example of a database 600 including auditing fields and meta data provided by system 100. In this instance, a meta data column 602 indicates to the user the color depth of the image for each available image, as well as an auditing field 604 showing when the item was last edited. In some embodiments, it may be more appropriate to use a structure including a separate audit table, with a foreign key reference, to provide greater flexibility in handling multiple audit events. In such instance, database 600 provides a unique key that cross-references to corresponding fields in the auditing table. Such structure facilitates handling of multiple events (e.g., multiple histories of edits rather than just the latest edit).

Figure 7:
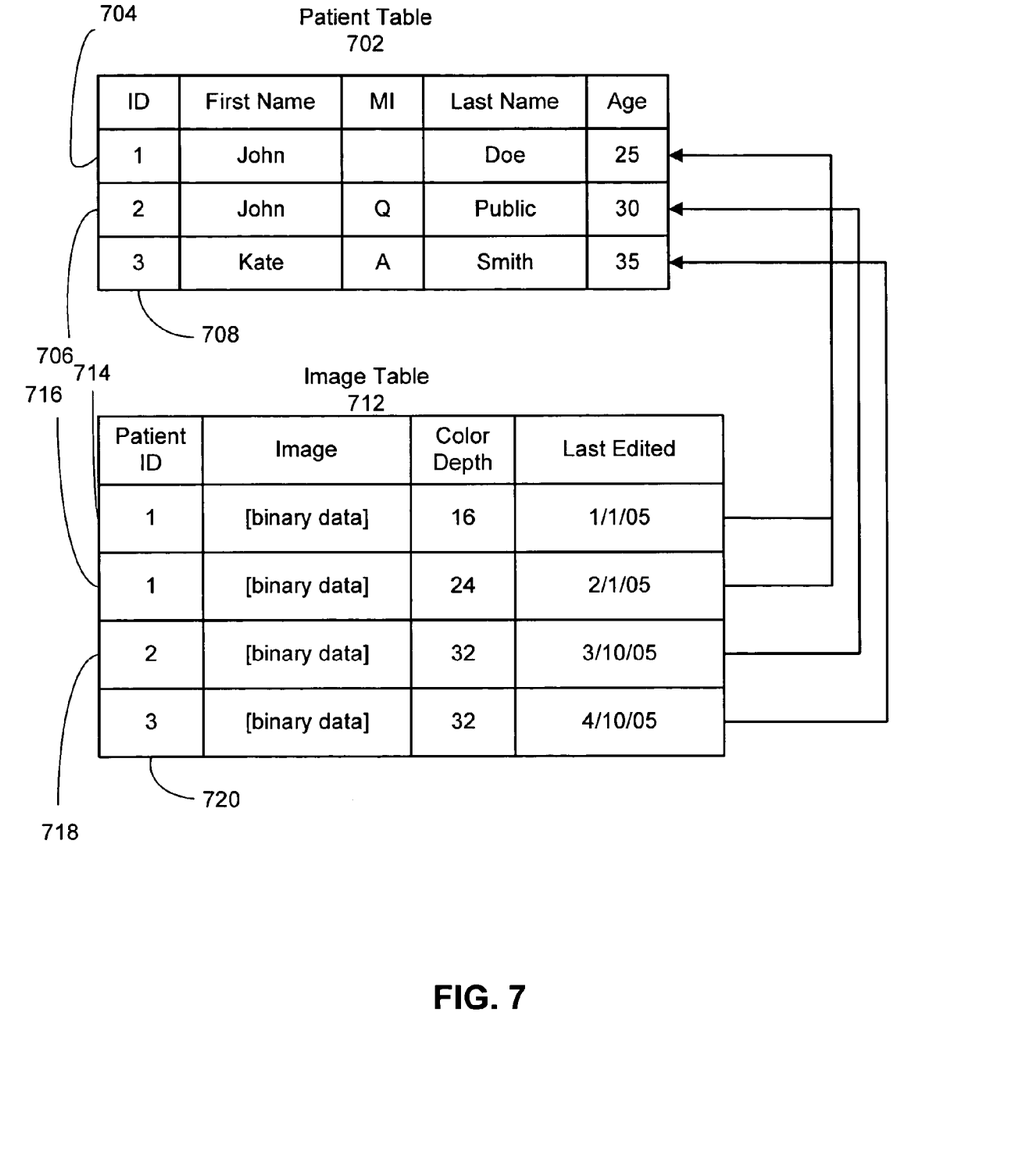
FIG. 7 illustrates a normalized database schema in accordance with the present invention.

Referring also now to FIG. 7, a patient table 702 allowing access to patient information makes use of an image table 712 to provide patient images and data. In this instance, three patient rows 704-708 for patient table 702 are derived from four image rows 714-720. Because multiple images (of varying quality and differing dates) are available for one of the patients, information from image rows 714 and 716 are both associated with a single patient row 704. In one embodiment, image tables are subdivided into separate Study, Series, and Image(s) tables. However, any manner of structuring the information so that it is readily and unambiguously stored and accessed can be used in accordance with the present invention.

Figure 8:
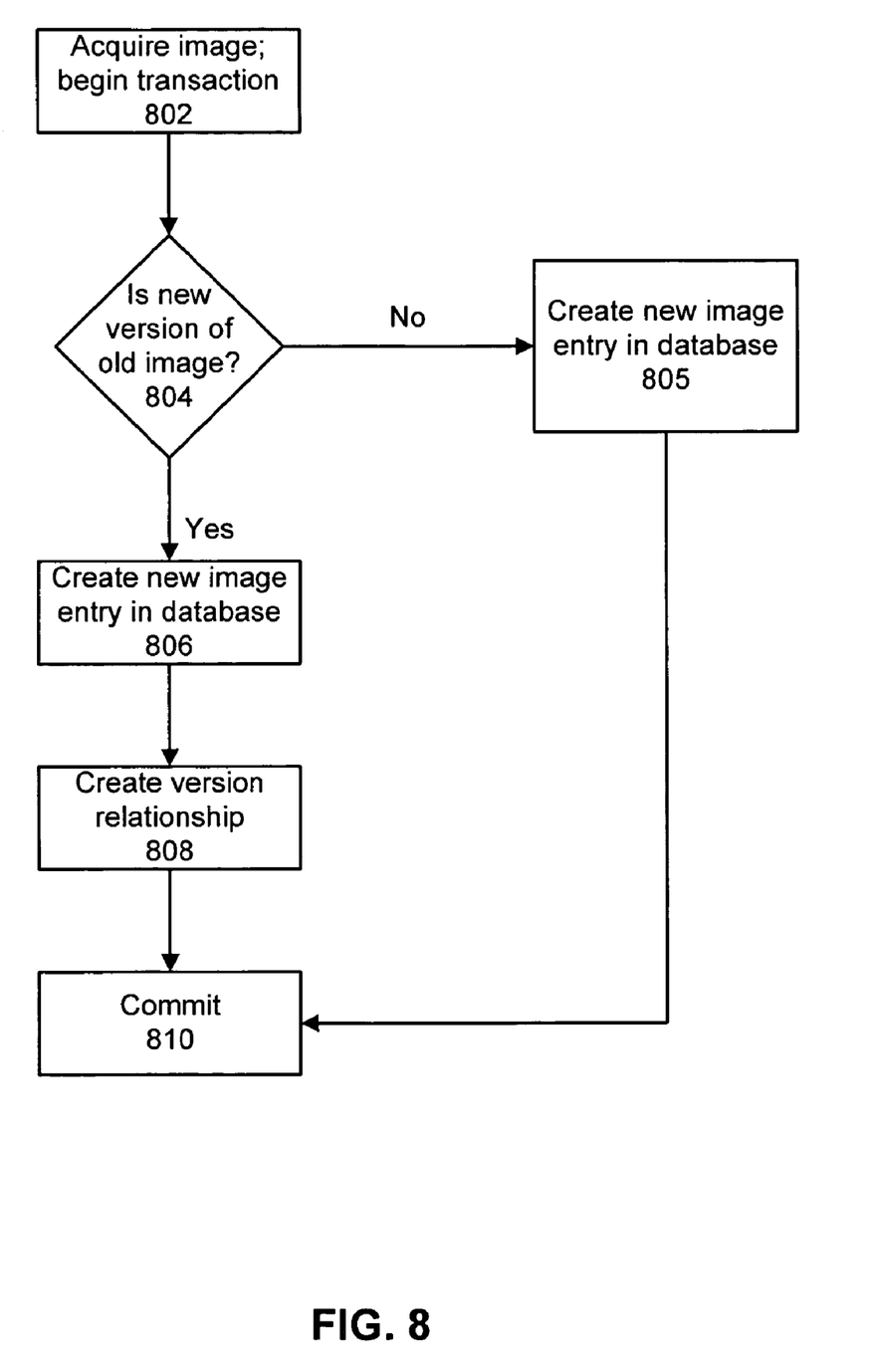
FIG. 8 illustrates a workflow for versioning of images in accordance with the present invention.

Referring now to FIG. 8, there is shown processing for adding image information with versioning information in accordance with a preferred embodiment. Processing commences with acquiring an image and thereby beginning the transaction 802. A check 804 is then made to determine whether the acquired image is a new version of an old image. If not, a new image database entry is created 805. If so, a new image entry is created 806 as well as a new version relationship 808. In either instance, the commit procedure is then undertaken 810.

Figure 9:
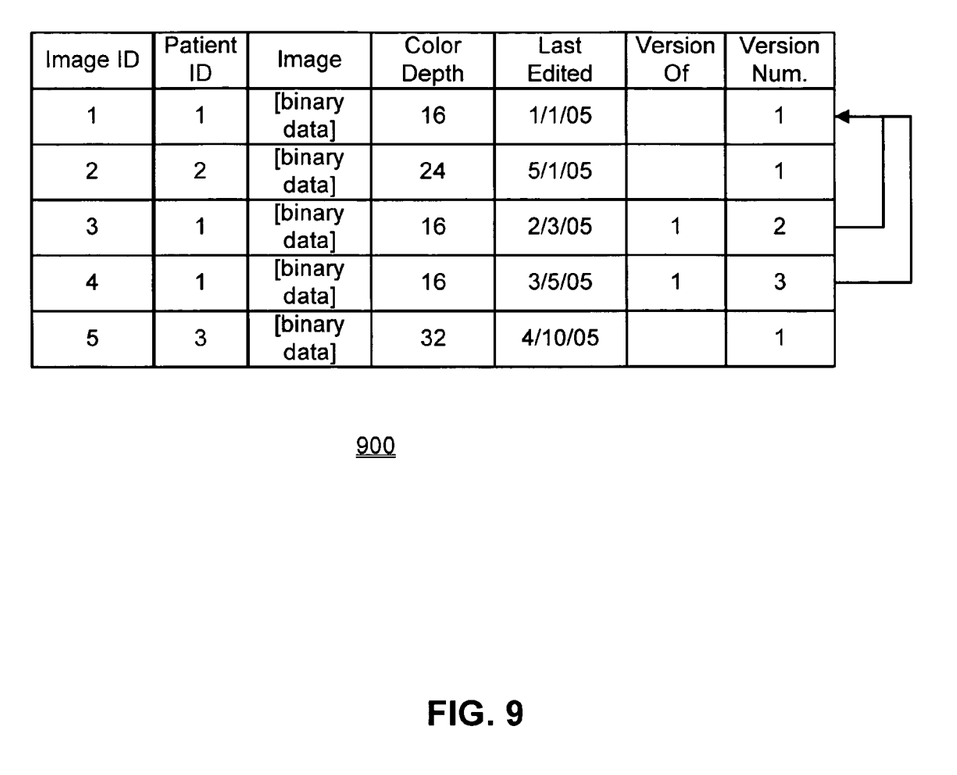
FIG. 9 illustrates an image table showing relationships among different image versions.

Referring now to FIG. 9, there is shown a database 900 illustrating the results of the processing described in connection with FIG. 8, in that three versions of an image for a particular patient are stored in database 900. In this example, a "User ID" column is included to indicate who was responsible for the last edit.

Figure 10:
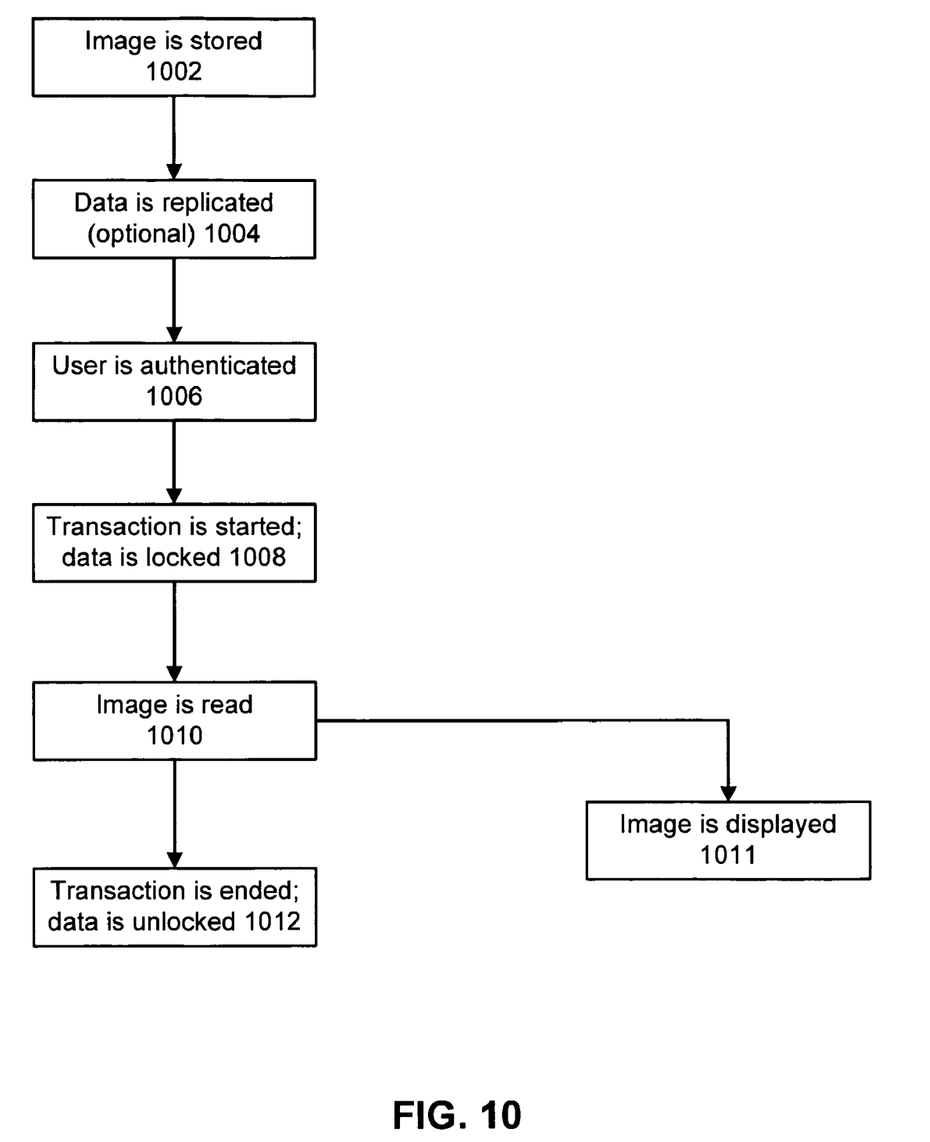
FIG. 10 illustrates an image retrieval workflow, including locking to prevent multiple clinicians/providers from performing the same interpretation, in accordance with the present invention.

Referring now to FIG. 10, a workflow for image retrieval in accordance with a preferred embodiment is disclosed. Processing here begins with storage 1002 of an image and, depending on the data robustness desired by the application, replication 1004 of the data. A user seeking to retrieve an image is authenticated 1006, a transaction is started 1008 thereby locking the image data to prevent, for example, two radiologists from reading a study at once. The image is then read 1010, displayed 1011 and concurrently the transaction is concluded with the data being unlocked 1012.

Figure 11:
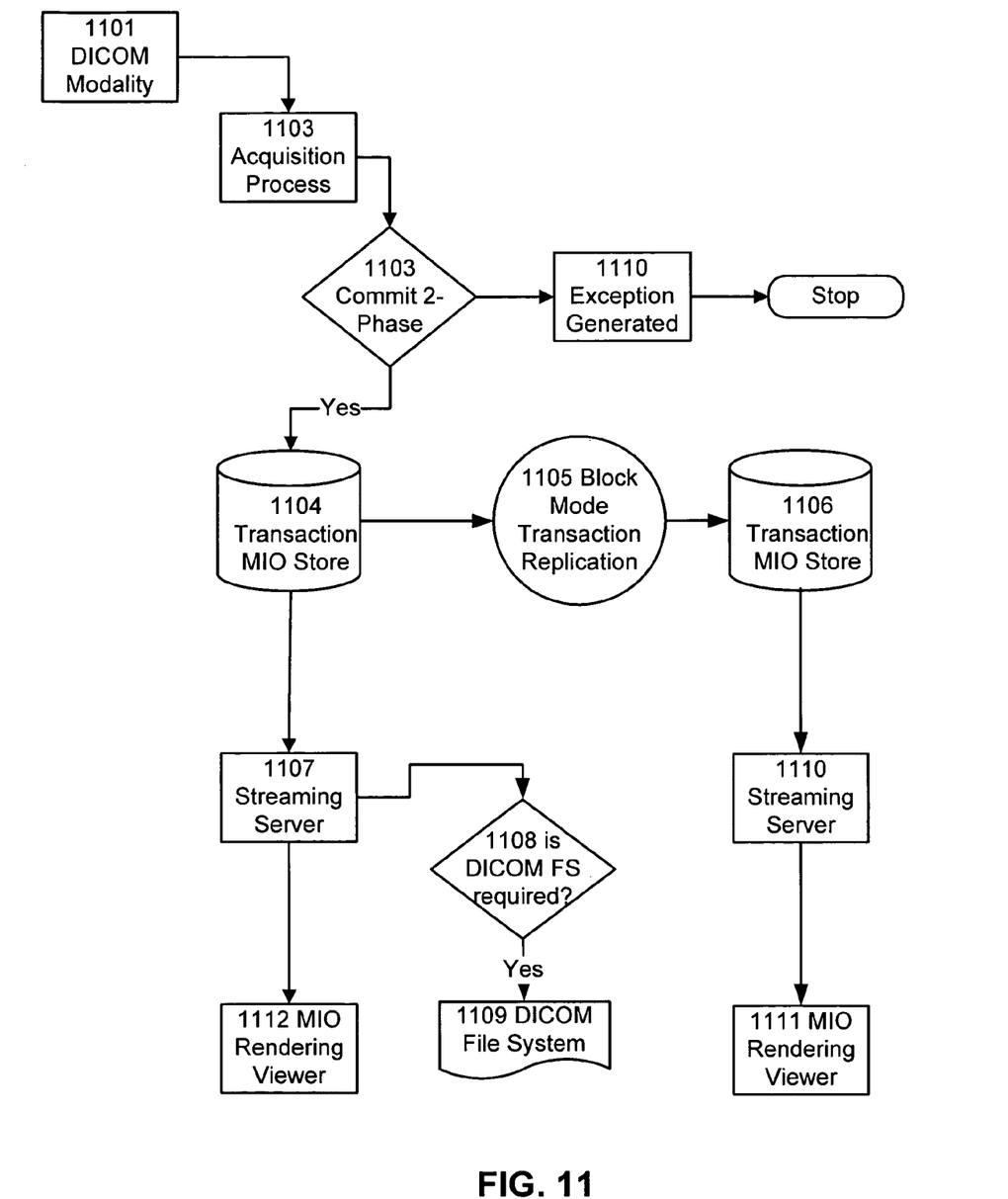
FIG. 11 illustrates a functional workflow of image management in accordance with the present invention.

Referring now to FIG. 11, there is shown a functional workflow of image management in accordance with a preferred embodiment, summarizing one application of the discussion above. In this example, a DICOM modality 1101 serves as the imaging source, on which acquisition process 1103 operates to obtain image data. A two-phase commit process 1103 is attempted; if not successful an exception is generated 1110 and processing stops. Otherwise, a medical image object store transaction 1104 commences, with communication to a streaming server 1107, medical image object rendering viewer 1112 and, if DICOM file storage is required 1108, storage in DICOM file system 1109. In this example, block mode transaction replication 1105 is used, in which a replicated image object store transaction 1106 commences, with communication to streaming server 1110 and medical image object rendering viewer 1111.

Upon reading this disclosure, those of skill in the art will appreciate still additional alternative structural and functional designs for a system and process for transactional storage and workflow routing for medical image objects. Thus, while particular embodiments and applications of the present invention have been illustrated and described, it is to be understood that the invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as described in the appended claims.

What is claimed is:

1. A Picture Archiving and Communications System, comprising:
   an imaging modality subsystem configured to produce medical images;
   a PACS workstation communicatively coupled with the imaging modality subsystem to process data corresponding to the medical images; and
   a database subsystem communicatively coupled with the imaging modality subsystem and the PACS workstation, the database subsystem including a processor configured to process the medical images and the data corresponding to the medical images, wherein the database subsystem is a relational database that uses two-phase commit processing to store the medical images in a storage medium, wherein two-phase commit processing includes storing multiple instances of an image and images of the same body part,
   and further wherein the database subsystem is configured to ensure transactional integrity of the medical images and the data corresponding to the medical images by use of commit/rollback processing in which a transaction results in commit processing if possible and rollback processing if commit processing fails.

2. A Picture Archiving and Communications System as in claim 1, wherein the database subsystem stores the medical images in the storage medium so as to provide atomicity, consistency, isolation and durability (ACID) characteristics.

3. A Picture Archiving and Communications System as in claim 1, wherein the database subsystem is a distributed system.

4. A Picture Archiving and Communications System as in claim 1, wherein the database subsystem includes an exception handler configured to utilize the processor to process the medical images and the data corresponding to the medical images responsive to a failure of two-phase commit processing.

5. A Picture Archiving and Communications System as in claim 1, wherein the data corresponding to the medical images includes at least one of a subset of patient name, exam information, timestamp, patient medical record, image meta data, image version, image size, image quality, color depth, edit history, user identification, and audit information.

6. A computer implemented method of transitionally storing medical images and routing workflows for the medical images comprising:
   communicating the medical images to a storage database;
   communicating data corresponding to the medical images to the storage database; and
   processing the medical images and the data corresponding to the medical images to store the medical images and the data corresponding to the medical images in the storage database with transactional integrity, wherein the processing includes two-phase commit processing to store the medical images, wherein two-phase commit processing includes storing multiple instances of an image and images of the same body part,
   and further wherein the storage database is configured to ensure transactional integrity of the medical images and the data corresponding to the medical images by use of commit/rollback processing in which a transaction results in commit processing if possible and rollback processing if commit processing fails.

7. A method as in claim 6, wherein the step of processing includes atomicity, consistency, isolation and durability (ACID) characteristics.

8. A method as in claim 6, further comprising the step of distributing the database among a plurality of servers.

9. A method as in claim 6, wherein the processing includes exception handling to process the medical images and the data corresponding to the medical images responsive to a failure of two-phase commit processing.

10. A method as in claim 6, wherein the data corresponding to the medical images includes at least one of a subset of patient name, exam information, timestamp, patient medical record, image meta data, image version, image size, image quality, color depth, edit history, user identification, and audit information.

11. A method as in claim 6, wherein processing includes commit/rollback processing in which a transaction results in commit processing if possible and rollback processing if commit processing fails.

* * * * *

UNITED STATES PATENT AND TRADEMARK OFFICE
CERTIFICATE OF CORRECTION

| | | |
|---|---|---|
| PATENT NO. | : 7,574,452 B2 | Page 1 of 1 |
| APPLICATION NO. | : 11/288956 | |
| DATED | : August 11, 2009 | |
| INVENTOR(S) | : Ronald Keen | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 425 days.

Signed and Sealed this

Seventh Day of September, 2010

David J. Kappos
*Director of the United States Patent and Trademark Office*